United States Patent [19]

Kubicek

[11] 4,059,636

[45] Nov. 22, 1977

[54] MERCAPTANS BY CATALYTIC CLEAVAGE OF ORGANIC SULFIDES

[75] Inventor: Donald H. Kubicek, Bartlesville, Okla.

[73] Assignee: Phillips Petroleum Company, Bartlesville, Okla.

[21] Appl. No.: 682,934

[22] Filed: May 4, 1976

[51] Int. Cl.$^2$ .................................... C07C 148/00
[52] U.S. Cl. ............................ 260/609 D; 260/609 R
[58] Field of Search ............ 260/609 B, 609 D, 609 R

[56] References Cited

U.S. PATENT DOCUMENTS

| | | | |
|---|---|---|---|
| 2,402,614 | 6/1946 | Farlow et al. | 260/609 R |
| 2,829,171 | 4/1958 | Dovmani | 260/609 R |
| 3,069,472 | 12/1962 | Loev et al. | 260/609 R |
| 3,143,574 | 8/1964 | Brown | 260/609 R |
| 3,214,386 | 10/1965 | Warner et al. | 260/609 R |
| 3,231,488 | 1/1966 | Gatsis et al. | 260/609 R |
| 3,880,933 | 4/1975 | Kubicek | 260/609 R |

*Primary Examiner*—Delbert R. Phillips

[57] ABSTRACT

A method is provided for preparing mercaptans by catalytic cleavage of organic sulfides with hydrogen sulfide in the presence of a supported phosphotungstic acid catalyst. The process is particularly advantageous with n-alkyl sulfide feedstock and being highly selective for producing n-alkyl mercaptan product. In one embodiment the presence of carbon disulfide in the reaction mixture increases the conversion at low temperature as compared to the process without the presence of carbon disulfide.

8 Claims, No Drawings

MERCAPTANS BY CATALYTIC CLEAVAGE OF ORGANIC SULFIDES

BACKGROUND OF THE INVENTION

This invention pertains to the preparation of mercaptans. In a more specific aspect of this invention it pertains to the preparation of mercaptans by the cleavage reaction of organic sulfides with hydrogen sulfide. In another of its aspects this invention relates to the catalyzed cleavage of organic sulfides. In yet another of its aspects this invention relates to the cleavage of n-alkyl sulfides. In yet another aspect of this invention it pertains to the improvement in the conversion of reactants in the process of preparing mercaptans from the cleavage reaction of organic sulfides with hydrogen sulfide in the presence of a sulfactive catalyst.

It is well known in the art to prepare mercaptans by the cleavage of organic sulfides with hydrogen sulfide in the presence of a sulfactive catalyst. This reaction has been modified by the use of various promoters for the catalysts and by the presence of modifying compounds along with the reactants. It has been found, however, that the cleavage reaction of n-alkyl sulfides is difficult with conventionally used catalysts. The cleavage of n-alkyl sulfides requires higher temperature than does the cleavage of secondary and tertiary sulfides. This causes the cleavage reaction of normal alkyl sulfides to lead to more by-products which are difficult to separate and which can be undesirable for other reasons.

A catalyst has now been discovered with which higher conversion and higher selectivity can be obtained in the cleavage of organic sulfides to the corresponding mercaptans using hydrogen sulfide. Higher conversion and higher selectivity in the reaction of normal alkyl sulfides has been noted particularly. It has also been discovered that the presence of carbon disulfide in the reaction mixture enhances the conversion of reactants to the desired mercaptan products.

It is, therefore, an object of this invention to provide a method for improving the conversion and selectivity in mercaptan product in the cleavage of organic sulfides with hydrogen sulfide.

Other aspects, objects and the various advantages of this invention will become apparent upon reading of the specification and the appended claims.

STATEMENT OF THE INVENTION

According to the present invention, in the preparation of mercaptans by catalytic cleavage of organic sulfides with hydrogen sulfide the presence of a supported phosphotungstic acid catalyst provides a method for increasing the total conversion and selectivity of reactants to mercaptans.

According to one embodiment of this invention, in the preparation of mercaptans by cleavage of organic sulfides with hydrogen sulfide in the presence of a supported phosphotungstic acid catalyst a method for increasing the total conversion of reactants to mercaptans is provided by adding carbon disulfide to the reaction mixture.

The organic sulfides useful in the practice of this invention include those of general formula R-S-R; wherein the R groups are independently selected from a group consisting of alkyl, cycloalkyl, aromatic, alkyl-aryl, arylalkyl, straight chain or branched chain with the R's being the same or different in the same molecule and with the R group selected so that the useful sulfides generally contain from about 2 to about 40 or more carbon atoms per molecule with a preferable range of carbon atoms being from about 2 to about 16.

Examples of useful sulfides include dimethyl sulfide, diethyl sulfide, diisopropyl sulfide, di-n-butyl sulfide, di-n-octyl sulfide, di-n-dodecyl sulfide, di-n-eicosyl sulfide, methyl ethyl sulfide, n-pentyl-n-heptyl sulfide, dicyclohexyl sulfide, bis(4-methylcyclohexyl) sulfide, diphenyl sulfide, di-p-tolyl sulfide, bis(p-n-hexylphenyl) sulfide, dibenyl sulfide, and the like. Mixtures of sulfides as feedstock as well as mixtures of sulfide with other inert components are within the scope of this invention.

Instead of using the usual commercial catalyst of either molybdenum oxide, cobalt oxide, or cobalt molybdate on alumina, the present invention uses a catalyst of phosphotungstic acid and thereby obtains higher conversion and higher selectivity as compared to the prior art catalyst. The phosphotungstic acid catalyst can be deposited on such well-known supports as activated carbon, alumina, zirconia, silica, thoria, pumice, and silica-alumina compositions, but at present the preferred support is alumina.

Hydrogen sulfide is employed in this invention in amounts sufficient to give the desired degree of cleavage of the organic sulfide feedstock. Hydrogen sulfide/organic sulfide mole ratios generally in the range of about 1/1 to about 40/1 and preferably about 1.5/1 to about 30/1 are employed.

The use of any amount of carbon disulfide will affect the reaction so that carbon disulfide is employed in this invention in an amount sufficient to produce the desired effect on the reaction. Generally organic sulfide/carbon disulfide mole ratios in the range about 0.1/1 to about 50/1 and preferably about .25/1 to about 10/1 produce the desired results.

If desired, an inert diluent can be employed in the feedstream to dilute or fluidize the feedstream. Such diluents may be especially desirable with higher molecular-weight organic sulfide to facilitate flow to and from the reactor. Such diluents include hydrocarbons such as pentane, hexane, benzene, toluene, xylenes, etc. They can be used in any suitable amounts.

The above-described ingredients of the feedstream are intimately mixed by any means well known in the prior art and are then contacted with the catalyst in any suitable reaction zone under any suitable sulfide-cleaving conditions which produce the desired results. This invention is especially well suited for use of a continuous reactor, but, if desired, a batch reactor can be employed.

Reaction temperatures can vary widely depending on other reaction conditions, as well as, on the reactivity of the sulfide feedstock and on the degree of sulfide cleavage desired. Generally, temperatures in the range of about 350° to about 700° F (177° to 371° C) are employed using presently available commercial catalysts. The use of the phosphotungstic acid catalyst permits good conversion of selectivity in a temperature range of about 350 to about 600° F (177° to 315° C), though it is prefereable because of rate, side-reactions, etc., to employ temperatures in the range of about 450 to about 550° F (232° to about 288° C).

Reaction pressures can vary widely. Usually pressures in the range of about 100 to about 5000 psig can be used, though, as a matter of convenience, pressures of about 150 to about 750 psig are normally preferred.

Contact time of the reactants with catalyst under suitable sulfide-cleaving conditions can vary widely depending on desired degree of sulfide-cleavage and other reaction conditions; however, weight hourly space velocities (weight feed/weight catalyst/hour) in the range of about 0.1 to about 10 and preferably about 0.4 to about 2 are normally employed.

EXAMPLE I

Preparation of the Catalyst 1.0 g phosphotungstic acid (Mallinckrodt $P_2O_5 \cdot 24WO_3 \cdot XH_2O$) was dissolved in 100 ml. distilled water and 50 g alumina ($Al_2O_3$) was added and thoroughly stirred to insure complete contact of the fresh acid solution with the support. The water was stripped and the catalyst was dried at 260° C for 2 hours in a stream of $H_2S$. No further activation was required.

EXAMPLE II

Cleavage of n-dibutyl sulfide

A stainless steel tubular reactor with heaters ($\frac{1}{2}$ × 18 inch diameter × length) was charged with 10 ml. glass beads, 50 g (70 ml.) of catalyst as prepared in Example I and another 10 ml. layer of glass beads. The reactor was heated to the operating temperature and pressurized with $H_2S$ at 450 or 500 psig. n-Dibutyl sulfide was fed at the rate of 3.0 ml./minute. 810 g $H_2S$, 348 g sulfide, and, optionally 6 g of $CS_2$ were passed through the apparatus. The results are tabulated below:

Table I

| T° C | Conversion of sulfide % No $CS_2$ present in the feed | Conversion with 6 g of $CS_2$ present in the Feed % |
|---|---|---|
| 204 | 6.4 | 7.8 |
| 232 | 8.1 | 28.7 |
| 260 | 23.4 | 69.2 |
| 288 | 61.2 | 79.1 |
| 315.5 | 73.9 | 87.9 |

The data show good conversion at 288° C and 315° C. There is considerable improvement if $CS_2$ is present in the feed as promoter.

EXAMPLE III

A series of comparison runs was made using the catalyst of this invention and conventional catalysts known in the art. The feed was 0.28 moles n-dibutyl sulfide, 2.8 moles $H_2S$, 0.09 moles $CS_2$ per hour of operation. The results are tabulated below.

Table II

| Catalyst Used | Temperature | % Conversion/pass | % Selectivity to n-$C_4$SH |
|---|---|---|---|
| Cobalt Molybdate | 500° F (260° C) | 59.1 | 64.4 |
| Cobalt Molybdate | 550° F (288° C) | 80.3 | 33.9 |
| Cobalt Oxide on $Al_2O_3$ | 500° F | 24.0 | 59.6 |
| Cobalt Oxide on $Al_2O_3$ | 550° F | 65.5 | 77.2 |
| Phosphotungstic Acid on Alumina (Invention) | 500° F | 71.5 | 91.5 |
| Phosphotungstic Acid on Alumina (Invention) | 550° F | 81.2 | 79.2 |

The data show that phosphotungstic acid catalyst has a higher conversion and selectivity than either of the two other catalysts; especially at the lower temperature of 260° C, the selectivity is quite high.

EXAMPLE IV

Another series of tests was made using di n-dodecyl sulfide feed. The di n-dodecyl sulfide contained some isomeric constituents; conversions and selectivities are calculated on total of all $C_{12}$ fractions which are not clearly separated by GLC analysis.

Feed in moles/hour of operation:
0.14 moles di n-dodecyl sulfide
1.40 moles $H_2S$
0.11 moles $CS_2$
0.45 moles $C_6H_6$ The runs are summarized below.

Table III

| Catalyst Used | Temperature | % Conversion/pass | % Selectivity to $C_{12}SH$ |
|---|---|---|---|
| Cobalt Molybdate | 450° F (232° C) | 21.4 | 77.2 |
| Cobalt Molybdate | 500° F (260° C) | 44.7 | 59.3 |
| Cobalt Molybdate | 550° F (288° C) | 82.3 | 26.0 |
| Phosphotungstic Acid | 450° F | 29.7 | 87.6 |
| Phosphotungstic Acid | 500° F | 47.0 | 74.7 |
| Phosphotungstic Acid | 550° F | 75.3 | 51.6 |

The data show that conversion and selectivity are higher using the catalyst of this invention, phosphotungstic acid on alumina, especially at the lower temperatures of 232° C and 260° C. The drop in selectivity at 288° C is due to a side reaction mentioned earlier.

Thus, the new catalyst has been shown to be effective in converting organic sulfides to the corresponding mercaptans, especially for the more difficult conversion reaction of normal alkyl sulfides.

I CLAIM:

1. A method in which mercaptans are prepared by catalytic cleavage of organic sulfides with hydrogen sulfide in the presence of a supported phosphotungstic acid catalyst at a temperature and pressure sufficient for catalytic cleavage of organic sulfides.

2. A method of claim 1 wherein carbon disulfide is present in the reaction mixture.

3. A method of claim 1 wherein the reaction is carried out at a temperature ranging from about 177° C to about 315° C and the pressure is from about 100 to about 5000 psig.

4. A method of claim 2 wherein the carbon disulfide is added to the reaction mixture in a mole ratio in the range of about 0.1/1 to about 50/1 of organic sulfide/carbon disulfide.

5. A method of claim 1 wherein the organic sulfides are represented by the formula R-S-R; wherein the R groups are independently selected from the group consisting of alkyl, cycloalkyl, aromatic, alkylaryl, arylalkyl, straight chain or branched chain with the R's being the same or different in the same molecule and with the R group selected so that the useful sulfides contain from about 2 to about 40 or more carbon atoms per molecule.

6. A method of claim 5 wherein the organic sulfide is chosen from among the group comprising dimethyl sulfide, diethyl sulfide, diisopropyl sulfide, di-n-butyl sulfide, di-n-octyl sulfide, di-n-dodecyl sulfide, di-n-eicosyl sulfide, methyl ethyl sulfide, n-pentyl-n-heptyl sulfide, dicyclohexyl sulfide, bis(4-methylcyclohexyl) sulfide, diphenyl sulfide, di-p-tolyl sulfide, bis(p-n-hexylphenyl) sulfide, and dibenzyl sulfide.

7. A method of claim 1 wherein the phosphotungstic acid catalyst is supported on a metal selected from among activated carbon, alumina, zirconia, silica, thoria, pumice, and silica-alumina.

8. A method of claim 7 wherein said material is alumina.

* * * * *